United States Patent [19]

Vishnupad et al.

[11] Patent Number: 4,832,858

[45] Date of Patent: May 23, 1989

[54] WATER DISPERSIBLE PETROLEUM JELLY COMPOSITIONS

[75] Inventors: Mohan Vishnupad, Monroe; Jose E. Ramirez, Trumbull; Robert A. Bornfriend, Ridgefield, all of Conn.

[73] Assignee: Chesebrough-Pond's Inc., Greenwich, Conn.

[21] Appl. No.: 16,600

[22] Filed: Feb. 19, 1987

[51] Int. Cl.$^4$ .............................................. C10M 173/00
[52] U.S. Cl. ...................................... 252/49.5; 44/51; 252/11; 252/49.9; 252/52 A; 252/308; 514/786; 514/939; 514/941; 514/943
[58] Field of Search ...................... 252/11, 49.5, 52 A, 252/49.9, 308, 786; 514/939, 941, 943; 44/51

[56] References Cited

U.S. PATENT DOCUMENTS

| | | | |
|---|---|---|---|
| 2,617,754 | 11/1952 | Neely | 167/91 |
| 3,176,964 | 4/1965 | Cottell et al. | 261/1 |
| 3,228,842 | 1/1966 | Markland | 167/87 |
| 3,489,690 | 1/1970 | Lachampt et al. | 252/308 |
| 3,852,475 | 12/1974 | Tarangel | 424/361 |
| 3,926,413 | 12/1975 | D'Urso | 259/4 R |
| 3,957,971 | 5/1976 | Oleniacz | 424/70 |
| 4,035,514 | 7/1977 | Davis | 424/365 |
| 4,184,978 | 1/1980 | France et al. | 252/309 |
| 4,216,201 | 8/1980 | Calvo | 424/63 |
| 4,218,221 | 8/1980 | Cottell | 44/51 |
| 4,244,702 | 1/1981 | Alliger | 44/51 |
| 4,284,630 | 8/1981 | Yu et al. | 514/937 |
| 4,395,266 | 7/1983 | Han | 44/51 |
| 4,407,824 | 10/1983 | Eckert | 514/939 |
| 4,422,952 | 12/1983 | Koulbanis et al. | 252/309 |
| 4,618,441 | 10/1986 | Tsai | 252/49.5 |
| 4,654,155 | 3/1987 | Kipp et al. | 252/49.5 |
| 4,690,774 | 9/1987 | Vishnupad et al. | 252/309 |

FOREIGN PATENT DOCUMENTS 1127039  7/1982  Canada .

OTHER PUBLICATIONS

Colloid Chemistry Theoretical & Applied, vol. V, J. Alexander, ed., (1944), pp. 346–351, Emulsification and Emulsions and Sonic and Ultrasonic Waves.
"Influence of Power on Quality of Emulsions Prepared by Ultra-Sound", Higgins, D. M. et al., J. of Pharmaceutical Sciences, vol. 61, #10, 10-1972, pp. 1567–1570.
Cosmetic and Toiletry Formulations, Flick, E. W., pp. 225–226, Noyes Publications, Mass., 1984.
Ultrasonic Emulsification, McCarthy, W. W. Ph. D., 1964, pp. 821–824 and 920.
Chemical Abstracts, vol. 99, 27934P (1983), A Comparative Study of Emulsions Prepared by Ultrasound & by a Conventional Method.
Chemical Abstracts, vol. 76, 63643b(1972), Emulsions Preparation in an Ultrasonic Field I. Diluted Emulsions of the Oil/H$_2$O Type.

*Primary Examiner*—William R. Dixon, Jr.
*Assistant Examiner*—Margaret B. Medley
*Attorney, Agent, or Firm*—Melvin H. Kurtz

[57] ABSTRACT

A stable, water dispersible petroleum jelly formulation, which is an oil-in-water emulsion, is described which comprises water, petroleum jelly, optional humectant, and emulsifier. The composition is formed by ultrasonically emulsifying the various components which will ultimately form the emulsion.

16 Claims, No Drawings

WATER DISPERSIBLE PETROLEUM JELLY COMPOSITIONS

BACKGROUND OF THE PRESENT INVENTION

1. Field of the Invention

The present invention relates of petroleum jelly compositions (oil-in-water emulsions) which are easily dispersible in water.

Description of the Prior Art

It is taught in U.S. Pat. No. 3,852,475 that the inclusion of hydrophobic starch in topical compositions containing solid petroleum jelly reduces the greasy appearance and feel normally associated with such compositions as well as reducing the resistance of the compositions to washing with cold water soap and detergent compositions. The compositions that are shown in this patent contain no aqueous phase, are not emulsions, and are, moreover, apparently not dispersible in water. Similarly, U.S. Pat. No. 4,035,514 indicates that petroleum jelly containing up to 30%, by weight, of a combination dispersing agent comprising cetyl alcohol, lanolin alcohols and alkoxylated fatty acid esters of sorbitol can be dispersed in water without the use of additional soaps or detergents. Once again, this reference relates to petroleum jelly compositions which do not contain a water phase since they are described as viscous salves or creams. The compositions shown in this patent are merely designed to be dispersed in water and consist of an oil phase in combination with the dispersing agent only.

Cosmetic and Toiletry Formulations by E. W. Flick, on page 225, illustrates a cream comprising petrolatum, emulsifier, and water which is characterized as "oily" and "not dispersible in water".

Drug and Cosmetic Industry, Vol. 94, No. 6, June 1964, pages 821–824 and 920 mentions use of an ultrasonic emulsifier to produce a product called "Dry Skin Cream" (for Chesebrough-Pond's Inc.) which differs from the types of compositions which are part of the present invention in the following major ways: The resulting composition was a non-stable water-in-oil emulsion (rather than an oil-in-water emulsion) containing very low amounts (e.g., about 10% or so) of petroleum jelly; and, if added to water, such a composition would not readily disperse to form a milky white composition containing petroleum jelly of micron and submicron size.

For more than one year preceding the filing of this specification, a product was commercially available as VASELINE Extra Strength and VASELINE Dermatology Grade from Chesebrough-Pond's Inc. which is an oil-in-water emulsion containing low levels (e.g., 1–15%) petroleum jelly. The emulsion of this type utilized differing emulsifiers from those employed herein and was not formed by ultrasonic emulsification. If the materials used to form the emulsion were ultrasonically emulsified, the present inventor found that no stable, water dispersible oil-in-water emulsion was formed.

DESCRIPTION OF RELATED DEVELOPMENTS

Certain high oil-containing anhydrous foamable compositions are described in co-pending U.S. Ser. No. 774,728, filed Sept. 11, 1985, which comprise a petroleum jelly oil component in combination with a mild detergent component of such nature and in such amount for imparting foaming characteristics when the composition is subsequently combined with water. The anhydrous base compositions shown in the co-pending application do not contain a water phase.

Certain novel translucent water-in-oil emulsions containing petroleum jelly are described in co-pending U.S. Ser. No. 774,727, filed Sept. 11, 1985 allowed. These water-in-oil emulsions have the same general appearance and feel as petroleum jelly. They comprises an aqueous phase containing a humectant, an oil phase comprising petroleum jelly or petroleum jelly modified with mineral oil, and a water-in-oil emulsifying agent. These water-in-oil emulsions are, however, not dispersible in water.

More recently, copending U.S. Ser. No. 941,131, filed Dec. 12, 1986 ABN, entitled "Water Rinsable Petroleum Jelly Compositions", filed by M. Vishnupad et al., describes water rinsable petroleum jelly compositions which are water-in-oil emulsions comprising an aqueous phase containing humectant and surface active detergent, an oil phase of petroleum jelly, and a water-in-oil emulsifying agent. These compositions are not oil-in-water emulsions having the water dispersible characteristics of the instant compositions.

SUMMARY OF THE PRESENT INVENTION

The present invention is a stable, readily water dispersible petroleum jelly oil-in-water emulsion which comprises water, petroleum jelly, humectant (as an optional, but preferred ingredient), and emulsifier. The emulsion is made and is made stable by processing the various ingredients forming it through an ultrasonic emulsifier. The particle size of the oil phase in the present emulsions is predominantly of micron and submicron size.

The compositions of the present invention are oil-in-water emulsions which are stable (i.e., do not separate upon standing) and which are readily water dispersible in water. The term "water dispersible" as used herein is intended to indicate that when these emulsions are added to a larger volume of water, they form a milky white, substantially uniform dispersion of petroleum jelly particles of micron (e.g., up to only a few microns) and submicron size in the water upon being mixed therein. The instant emulsions, in preferred embodiments, can contain relatively high levels of petroleum jelly (e.g., about 30-about 60%, by weight).

DETAILED DESCRIPTION OF THE PRESENT INVENTION

The oil phase of the compositions of the present invention comprise petroleum jelly either in neat or modified form. Modified forms of petroleum jelly include those compositions where some of the petroleum jelly has been replaced by mineral oil. The petroleum jelly that is intended for use in a preferred embodiment is a purified mixture of semi-solid hydrocarbons obtained from petroleum, chiefly of the methane series having a white to faintly yellowish color, a density of from about 0.820–0.865, a melting point of from about 38°–54° C. and a refractive index of 1.460–1.474. The amount of the oil phase in the present emulsions can range anywhere from about 15% to about 70%, by weight, of the total weight of the emulsion of the present invention. The amount of petroleum jelly can range from about 30% to about 60%, by weight, for example, in preferred embodiments.

The aqueous phase of the present invention comprises water, an optional but preferred humectant, and an oil-in-water emulsifier which is effective to confer the water dispersible characteristics on the composition of the present invention as essential ingredients. Generally speaking the weight percentage of the aqueous phase can range anywhere from about 30% to about 85%, by weight, of the entire emulsion.

The amount of water which can be contained in the aqueous phase of the emulsions of the present invention can range from about 30% to about 85%, by weight, of the aqueous phase.

The optional, though preferred, humectant which can be present in the aqueous phase of the emulsion of the present invention are those which are generally used in skin care products. The humectant can be present from about 0% to about 90%, by weight, of the aqueous phase. Examples of suitable humectants include glycerine, propylene glycol, sorbitol, sucrose, and the alkali metal salts of pyrrolidone carboxylic acid.

The oil-in-water emulsifying agent which is an essential component of the present invention should be present at from about 2% to about 6%, by weight, of the aqueous phase. Representative, compatible emulsifying agents that can be utilized include the dialkanolamine alkyl phosphate emulsifiers such as the diethanolamine monoalkyl phosphate species which are complex mixtures of esters of phosphoric acid and long chain alkyl groups. A commercially available material of this type is available under the trademark AMPHISOL and is a complex alkyl phosphate of diethanolamine carrying CAS Registry No. 69331-39-1.

In accordance with the present invention it has been found necessary that the aforementioned components which make up the emulsion be processed through an ultrasonic emulsifier in order to insure production of a stable emulsion. Conventional emulsifying apparatus such as colloid mills and homomixers do not produce stable emulsions in accordance with the present invention. Generally speaking, the size of the petroleum jelly or modified petroleum jelly component in the continuous water phase should range anywhere from about 15% to about 70% in preferred embodiments. Appropriate ultrasonic emulsifier apparatus which can be used to make the emulsions of the present invention are known to persons of ordinary skill in the art. A preferred type of apparatus is available under the trademark SONOLATOR from Sonic Corp., Stratford, CT.

U.S. Pat. Nos. 3,926,413 and 3,176,964, both of which are incorporated herein by reference, illustrate the general construction details of the SONOLATOR apparatus. Stated simply, such an apparatus operates by the feeding ($\geq 200$ lbs. force/in$^2$), through a jet into a cavitation zone in the form of a thin flat liquid stream at velocities of $\geq 200$ ft./sec, where it impinges onto a fixed blade and forces the blade to resonate at its natural, ultrasonic, resonant frequency. Cavitation is induced along the leading edge of the blade and the shock waves caused by the collapse of the cavitation bubbles shatter the large liquid globules and produce fine homogenization.

A suitable generalized and preferred manufacturing procedure for the compositions of the present invention is as follows:

OIL PHASE PREPARATION

1. Petroleum jelly and glyceryl monostearate are heated (e.g., to 70° C.).
2. Propyl paraben is melted into the resulting oil phase.
3. The diethanolamine monoalkyl phosphate emulsifier is then added, and the resulting compositions is mixed until uniform.
4. Oil soluble humectant(s) are then added and mixture is resumed.

WATER PHASE PREPARATION

1. Water is heated to 70° C.
2. The water soluble ingredients are dissolved in the heated water and mixing is resumed.

After the above preparation of the respective water and oil phases, they are combined and processed in the following manner:

1. The water phase is added to the oil phase and is mixed until uniform, keeping the mixture hot (e.g., 70° C.).
2. The resulting mixture is passed once (or multiple times) through the ultrasonic emulsifier (SONOLATOR emulsifier apparatus) at sufficient pressure (e.g., 1500 psi) to give the desired viscosity.
3. The resulting emulsion is collected in a kettle, cooled (e.g., to 60° C.) and fragrance is then added.

The emulsions which are the subject of the present specification and claims are of the oil-in-water type and are readily dispersible in water. Their pH ranges from about 5.4 to 5.8 with the following typical preferred viscosity ranges depending upon the power and number of cycles of the compositions through the SONOLATOR apparatus:

| Initial (at room temperature) | |
| --- | --- |
| 1 cycle: | 975–2000 cps |
| 2 cycles: | 1000–3000 cps |
| 3 cycles: | 1700–3000 cps |

The compositions, in general, can have viscosities of from about 900 to about 3000 cps.

The Examples which follow set forth certain specific embodiments of the present invention.

EXAMPLE 1

The following ingredients were used to make a water dispersible petroleum jelly oil-in-water emulsion:

| Ingredient | Weight Percent |
| --- | --- |
| Petroleum jelly | 50.00 |
| Diethanolamine monoalkyl phosphate (AMPHISOL) | 3.00 |
| Glyceryl monostearate | 2.00 |
| Propyl paraben | 0.10 |
| Methyl paraben | 0.15 |
| Deionized water | 34.25 |
| propylene glycol | 10.00 |
| Bath oil fragrance | 0.50 |

The petroleum jelly and glyceryl monostearate were heated to 70° C. forming an oil phase mixture to which was then added the propyl paraben and diethanolamine monoalkyl phosphate (AMPHISOL). The resulting oil phase mixture was mixed until uniform.

The water was heated to 70° C. and the methyl paraben was dissolved therein. The propylene glycol was added to the resulting aqueous mixture and mixed into it forming an aqueous phase mixture.

The water phase mixture was added to the oil phase mixture and mixed for 20 minutes. The fragrance was added at 60° C. The resulting mixture was passed through an ultrasonic emulsifier (SONOLATOR brand) at 60° C. with a setting of 1500 psi on the emulsifier to yield a stable emulsion. It has been found that the use of temperatures below about 60° C. and the use of feed pressures of lower than 1500 psi in the apparatus utilized in this Example tended to produce unstable emulsions.

Emulsion stability can be further improved by passing the emulsion through the ultrasonic emulsifier more than once. The repeated emulsification produces higher viscosity emulsions without any substantial change in the water dispersible characteristics of the product.

The data given below reports the results of treating the composition of this Example to a variety of passes through the apparatus:

| No. of Passes | Initial Viscosity at 25° C. (cps units) |
| --- | --- |
| 1 | 1340 |
| 2 | 2080 |
| 4 | 3200 |
| 6 | 3910 |

EXAMPLE 2

The following ingredients were used to make another oil-in-water emulsion using the same general procedure described in Example 1.

| Ingredient | Weight percent |
| --- | --- |
| Petroleum jelly | 48.00 |
| Diethanolamine monoalkyl phosphate (AMPHISOL) | 3.00 |
| Glyceryl monostearate | 2.00 |
| Propyl paraben | 0.10 |
| Methyl paraben | 0.15 |
| Water | 34.25 |
| Acetylated lanolin alcohol (ACETULAN)* | 2.00 |
| Propylene glycol | 10.00 |
| Bath oil fragrance | 0.50 |

*heated with the petroleum jelly and glyceryl monostearate initially.

The above composition was subjected to ultrasonic emulsification under varying conditions:
A. One pass at 164° F. giving a composition having an initial viscosity of 225 cps. The overnight viscosity was 1630 cps and the overnight pH was 5.68.
B. One pass at 164° F. and one pass at 140° F. gave a composition having an initial viscosity of 875 cps. The overnight viscosity was 3610 cps and the overnight pH was 5.70.
C. One pass at 164° F. and three passes at 140° F. gave an initial viscosity of 1700 cps. The overnight viscosity was 5900 cps and the overnight pH was 5.60.
D. One pass at 164° F. and five passes at 148° F. produced an initial viscosity of 1300 cps. The overnight viscosity was 6600 cps and the overnight pH was 5.60.

The emulsions were acceptable and were easily dispersible in water.

EXAMPLE 3

The following formulation was made as previously described:

| Ingredient | Weight Percent |
| --- | --- |
| Petroleum jelly | 50.00 |
| Diethanolamine monoalkl phosphate (AMPHISOL) | 3.00 |
| Glyceryl monostearate | 2.00 |
| Propyl paraben | 0.10 |
| Methyl paraben | 0.15 |
| Water | 34.05 |
| Xanthan gum (KELTROL)* | 0.20 |
| Propylene glycol | 10.00 |
| Fragrance | 0.50 |

*mixed with the heated water prior to addition of the methyl paraben.

The resulting mixture was subjected to ultrasonic emulsification:

| A: | Passes: | 1 at 160° F. |
| --- | --- | --- |
|  | Initial Viscosity: | 1700 cps |
|  | Overnight Viscosity: | 5000 cps |
|  | Overnight pH: | 5.73 |
| B: | Passes: | 2 at 140° F. |
|  | Initial Viscosity: | 2900 cps |
|  | Overnight Viscosity: | 7150 cps |
|  | Overnight pH: | 5.75 |
| C: | Passes: | 4 at 144° F. |
|  | Initial Viscosity: | 2900 |
|  | Overnight Viscosity: | 8280 cps |
|  | Overnight pH: | 5.77 |

The emulsions were acceptable and were easily dispersible in water.

The foregoing Examples are intended to illustrate certain preferred embodiments of the present invention but should not be construed in a limiting sense. The scope of protection that is sought is set forth in the claims which follow.

What is claimed is:

1. A stable, water dispersible oil-in-water emulsion of petroleum jelly consisting essentially of: an aqueous phase, petroleum jelly and emulsifier said emulsion being prepared by ultrasonic emulsfication at a pressure above about 1500 p.s.i.g. and a temperature above about 60° C.

2. An emulsion as claimed in claim 1 which contains from about 15% to about 70%, by weight, of petroleum jelly.

3. An emulsion as claimed in claim 1 which contains from about 15% to about 70% by weight, petroleum jelly, from about 30% to about 85%, by weight of an aqueous phase, and from about 2% to about 6% emulsifier.

4. An emulsion as claimed in claim 3 wherein the emulsifier is a dialkanolamine alkyl phosphate emulsifier.

5. An emulsion of claim 1 additionally containing an humectant.

6. An emulsion of claim 1 additionally containing a fragrance.

7. An emulsion of claim 1 additionally containing an antimicrobial agent.

8. An emulsion of claim 1 additionally containing a thickener.

9. An emulsion of claim 1 additionally containing an humectant, a fragrance, an antimicrobial agent and a thickener.

10. A stable, water dispersible, oil-in-water emulsion of claim 1 consisting essentially of: from about 30% to 85% by weight of an aqueous phase consisting essentially of water and up to about 90% by weight of the aqueous phase, of a humectant, from about 15% to 70% by weight of petroleum jelly and from about 2% to about 6% by weight of a dialkanolamine alkyl phosphate emulsifier.

11. An emulsion of claim 10 additionally containing up to about 2% by weight of glycerol monostearate.

12. An emulsion of claim 10 additionally containing up to about 2% by weight of acetylated lanolin alcohol.

13. An emulsion of claim 10 additionally containing up to about 0.2% by weight of a gum thickener.

14. A method for forming a stable, water dispersible oil-in-water emulsion which comprises ultrasonically emulsifying, at a temperature above about 60° C. and a pressure above about 1500 psig, a mixture consisting essentially of water, petroleum jelly and and an aqueous phase emulsifier.

15. The method of claim 14 wherein the mixture comprises from about 15% to about 70%, by weight, petroleum jelly, from about 30% to about 85%, by weight, of an aqueous phase, and from about 2% to about 6%, by weight, emulsifier.

16. A method of claim 15 wherein the emulsifier is a dialkanolamine alkyl phosphate emulsifier.

* * * * *